United States Patent
Schwartz et al.

(10) Patent No.: US 6,503,878 B1
(45) Date of Patent: Jan. 7, 2003

(54) PELLETS

(75) Inventors: Curtis Schwartz, Ambler, PA (US); Steven Michael Baxter, Chalfont, PA (US)

(73) Assignee: Rohm and Haas Company, Philadelphia, PA (US)

( * ) Notice: Subject to any disclaimer, the term of this patent is extended or adjusted under 35 U.S.C. 154(b) by 64 days.

(21) Appl. No.: 09/667,646

(22) Filed: Sep. 22, 2000

Related U.S. Application Data

(60) Provisional application No. 60/156,080, filed on Sep. 24, 1999.

(51) Int. Cl.[7] ............................ C11D 3/37; C11D 11/02; C11D 17/00
(52) U.S. Cl. .................. 510/446; 510/224; 510/349; 510/361; 510/441; 510/443; 510/444; 510/452; 510/477; 510/533
(58) Field of Search ................... 510/224, 349, 510/361, 441, 443, 444, 446, 452, 477, 533

(56) References Cited

U.S. PATENT DOCUMENTS

| | | | | |
|---|---|---|---|---|
| 3,827,996 A | * | 8/1974 | Bereniewicz | 260/29.6 |
| 4,916,171 A | * | 4/1990 | Brown et al. | 523/161 |
| 4,921,898 A | * | 5/1990 | Lenney et al. | 524/459 |
| 5,360,567 A | * | 11/1994 | Fry et al. | 252/90 |
| 5,883,061 A | * | 3/1999 | Duccini et al. | 510/224 |
| 5,916,866 A | * | 6/1999 | Davies et al. | 510/441 |

FOREIGN PATENT DOCUMENTS

| | | | |
|---|---|---|---|
| EP | 576128 A1 | * | 12/1993 |
| EP | 711828 A2 | * | 5/1996 |
| EP | 716144 A2 | * | 6/1996 |
| EP | 896052 A1 | * | 2/1999 |
| EP | 972825 A2 | * | 1/2000 |
| EP | 1087009 A | * | 3/2001 |
| GB | 983243 | * | 2/1965 |
| GB | 989683 | * | 4/1965 |

OTHER PUBLICATIONS

Aldrich, "Thermal Transitions of Homopolymers: Glass Transition & Melting Point", Polymer Products from Aldrich, pp. 52 and 53. No Date Given.*

* cited by examiner

Primary Examiner—Yogendra N. Gupta
Assistant Examiner—Brian P. Mruk
(74) Attorney, Agent, or Firm—Stephen E. Johnson

(57) ABSTRACT

The present invention relates to pellets comprising one or more active ingredients; and either one or both of:
- (a) one or more binders incorporated within the body of the pellet; and
- (b) one or more coating materials on the surface of the pellet;

characterized in that either one or both of the binders and the coating materials comprise one or more polymers with a Tg in the range −85 to +35°C., and, optionally, wherein the coating and/or binder materials comprise at least one multi-phase polymer and further wherein at least one of the phases of the multi-phase polymer has a Tg in the range −85 to +35° C.

10 Claims, No Drawings

PELLETS

CROSS REFERENCE TO RELATED PATENT APPLICATIONS

This is a non-provisional application of prior pending U.S. provisional application Ser. No. 60/156,080 filed Sep. 24, 1999.

The present invention relates to pellets, particularly those which disintegrate quickly in aqueous media and which are sufficiently strong to withstand breakage during storage, shipping and handling.

By "pellet", we mean any solid formulation, including but not limited to, tablets, bricks, briquettes, bars, granules, balls, or blocks.

Pellets are well known in the fields of medicine and agriculture and more recently they are being used in detergent applications. Pellets offer certain advantages over granular compositions; they are non-dusting, do not require measuring, take up less space because they are compressed and the ingredients do not separate during transit and storage. However, problems are experienced regarding the dissolution or disintegration of the pellets in use as compared with granular compositions. In the manufacturing process, a balance must be kept between a pellet compacting pressure which is, on the one hand, high enough to ensure that the pellets are well formed and do not crumble during transport and storage, and a pellet compacting pressure which is, on the other hand, low enough to achieve an appropriate solubility/dispersibility profile. It is well known to use an additive to improve pellet dispersability, for example as disclosed in European Patent Application No. 99304428.8, and agents to improve the strength of the pellet so as to avoid the need for high pellet compacting pressure.

Looking specifically at agents which improve the strength of the pellet, GB 983,243 and GB 989,683 describe the use of a water-soluble organic film forming polymer to form on the pellet (briquette) surface a water soluble film which is sufficiently strong to help make detergent tablets resistant to abrasion and accidental breakage, when dry, and sufficiently soluble to help the detergent tablet to disintegrate readily in water. Suitable coating polymers are polyvinyl alcohol and polyvinyl acetate and, to a lesser extent, polyvinylpyrollidone, sodium carboxymethyl cellulose and hydroxypropyl methyl cellulose.

EP-A2-711828 teaches the use of a binder to improve the strength of detergent tablets; preferred binders are selected from polyethylene glycol, polyvinylpyrollidone, and polyacrylates and water soluble acrylate copolymers.

EP-A2-716144 teaches the use of the binders polyethylene glycol, polyvinylpyrollidone, and polyacrylates and water soluble acrylate copolymers in combination with an exterior coating of organic polymer. Suitable coating materials melt between 40 and 80° C. and preferably comprise a copolymer of (meth)acrylic acid and maleic acid or anhydride, or neutralised salts thereof.

EP-A1-896052 discloses detergent tablets with improved handling strength and swift dissolution which comprise a non-gelling binder and a coating. Examples of non-gelling binders are taken from the prior art but suitable coating materials are dicarboxylic acids for example selected from oxalic acid, malonic acid, succinic acid, glutaric acid, adipic acid, pimelic acid, suberic acid, azelaic acid, sebacic acid, undecanedioic acid, dodecanedioic acid, tridecanedioic acid and mixtures thereof.

Finally, U.S. Pat. No. 5,883,061 teaches polymeric tablet binders which comprise (meth)acrylic acid, maleic anhydride, alkyl (meth)acrylates, alkylhydroxy (meth)acrylates or styrene monomers in polymerised form. The polymer has a Tg of from +40 to +120° C. and a molecular weight of from 10,000 to 120,000.

The aim of the present invention is to provide novel pellets which are strong enough to be shipped, handled and stored without breakage and yet dissolve quickly on contact with water.

Accordingly, the present invention provides a pellet comprising: one or more active ingredients; and either one or both of (a) one or more binders incorporated within the body of the pellet; and (b) one or more coating materials on the surface of the pellet; characterised in that either one or both of the binder and coating materials comprise one or more polymers with a Tg in the range −85 to +35° C., and, optionally, wherein the binder and/or coating material comprise a multi-phase polymer and further wherein at least one of the phases of the multi-phase polymer has a Tg in the range −85 to +35° C.

It is not necessary for the binder materials and the coating materials to have the same polymer composition.

In a further embodiment of the present invention the pellet may comprise one or more binders with a Tg in the range −85 to +35° C. incorporated within the body of the pellet and a coating material on the surface of the pellet which may comprise one or more polymers with a Tg of greater than +30° C.

The polymers used in either one or both of the binder and coating materials of the present invention are mostly amorphous. The polymers used in the invention may be soluble or insoluble in water; those which are water insoluble are preferably readily dispersible in water. The binders and coating materials of the present invention comprise polymers with a Tg in the range −85 to +35° C. and preferably a Tg in the range from −60 to +10° C. These low Tg values are characteristic of "soft" polymers, that is, they will form a film or otherwise form an adhesive bond between the detergent granules within the pellet composition under the conditions of tablet manufacture, which, applicants believe, helps to maintain the integrity of the tablet from the point of manufacture, through storage, until used by the customer.

Such binder and/or coating polymers used in the present invention may comprise polymerized residues of one or more of the following monomers: (meth)acrylic acid, (meth)acrylate esters such as methyl (meth)acrylate, ethyl (meth)acrylate, butyl (meth)acrylate iso-butyl (meth)acrylate or t-butyl(meth)acrylate, 2-ethylhexyl (meth)acrylate, decyl (meth)acrylate iso-bornyl (meth)acrylate, and (meth)acrylate esters of alkylene glycols, polyalkylene glycols and (C1–C30) alkyl substituted polyalkylene glycols including esters of the formula CH2═CR1—CO—O(CH2CHR3O)m (CH2CH2CHR3O)nR2 where R1=H or methyl R2=H or C1–C30 alkyl R3=H or C1–C12 alkyl, m=0–40, n=0–40, and m+n is ≧1, such as hydroxyethyl (meth)acrylate, hydroxypropyl(meth)acrylate; C(1–30) substituted acrylamides; vinyl sulfonate, acrylamidopropanesulfonate; dimethylaminopropyl(meth)acrylamide, alkyl vinyl ethers, vinyl chloride, vinylidene chloride, N-vinylpyrollidone, allyl containing monomers; aromatic vinyl compounds such as styrene, substituted styrenes; butadiene; acrylonitrile; monomers containing acetoacetoxy functional groups such as acetoacetoxyethyl methacrylate; vinyl esters of saturated carboxylic acid, e.g., acetate, propionate, neodecanoate; acid or base containing monomers such as, for example, (meth)acrylic acid, itaconic acid, maleic acid, fumaric acid, N,N-dimethylaminoethyl methacrylate; or combinations thereof.

Additionally, crosslinking and grafting monomers such as 1,4-butyleneglycol methacrylate, trimethylolpropane triacrylate, allyl methacrylate, diallyl phthalate, divinyl benzene, or combinations thereof may be used. As used herein, by "(meth)acrylate" or "(meth)acrylic", we mean either acrylate or methacrylate for "(meth)acrylate" and acrylic or methacrylic for "(meth)acrylic".

The polymers used in the present invention may be made using known techniques, for example, solution, emulsion or suspension polymerisation. It is preferred that they are capable of being isolated in solid form, for example by spray drying. To facilitate this, they may comprise a multiphase polymer, that is, they have at least one phase which is relatively hard compared with another phase. Alternatively, a multiphase polymer dissolved or dispersed in water may also be used.

By "multi-phase" polymer we mean polymer particles with at least one inner phase or "core" phase and at least one outer or "shell" phase. The phases of the polymers are incompatible. By "incompatible" we mean that the inner and the outer phases are distinguishable using techniques known to those skilled in the art. For example the use of scanning electron microscopy and staining techniques to emphasise differences in the phases is such a technique.

The morphological configuration of the phases of the polymers may be for example, core/shell; core/shell particles with shell phases incompletely encapsulating the core; core/shell with a multiplicity of cores; or interpenetrating network particles.

The first phase may comprise a "soft" polymer with a Tg in the range −85 to +35° C., preferably a Tg in the range from −60 to +10° C. Such inner phase polymers may comprise polymerized residues of one or more of the following monomers: (meth)acrylic acid, (meth)acrylate esters such as methyl (meth)acrylate, ethyl (meth)acrylate, butyl (meth)acrylate iso-butyl (meth)acrylate or t-butyl(meth)acrylate, 2-ethylhexyl (meth)acrylate, decyl (meth)acrylate iso-bornyl (meth)acrylate, hydroxyethyl (meth)acrylate, hydroxypropyl(meth)acrylate; (meth)acrylate esters, for example, where the ester group is a polyalkyleneoxide or a C(1–30) alkoxylpolyalkyleneoxide; C(1–30) substituted acrylamides; vinyl sulfonate, acrylamidopropanesulfonate; dimethylaminopropyl(meth)acrylamide, alkyl vinyl ethers, vinyl chloride, vinylidene chloride, N-vinylpyrollidone, allyl containing monomers; aromatic vinyl compounds such as styrene, substituted styrenes; butadiene; acrylonitrile; monomers containing acetoacetoxy functional groups such as acetoacetoxyethyl methacrylate; vinyl esters of saturated carboxylic acid, e.g., acetate; propionate, neodecanoate; acid or base containing monomers such as, for example, (meth) acrylic acid, itaconic acid, maleic acid, fumaric acid, N,N-dimethylaminoethyl methacrylate. Additionally, crosslinking and grafting monomers such as 1,4-butyleneglycol methacrylate, trimethylolpropane triacrylate, allyl methacrylate, diallyl phthalate, divinyl benzene, or combinations thereof may be used.

The outer phase (sometimes regarded as a "shell" if it encapsulates the inner phase), of the multi-phase polymer may comprise either:

i) a polymer with a relatively high Tg value, for example from +40 to 160° C., which makes the outer phase relatively hard. The outer phase may comprise polymerized residues of one or more of the following monomers: (meth)acrylic acid, (meth)acrylate esters such as methyl (meth)acrylate, ethyl (meth)acrylate, butyl (meth)acrylate iso-butyl (meth)acrylate or t-butyl(meth)acrylate, 2-ethylhexyl (meth)acrylate, decyl (meth)acrylate iso-bornyl (meth)acrylate, hydroxyethyl (meth)acrylate, hydroxypropyl(meth)acrylate; (meth)acrylate esters, for example, where the ester group is a polyalkyleneoxide or a C(1–30) alkoxylpolyalkyleneoxide; C(1–30) alkylsubstituted acrylamides; vinyl sulfonate, acrylamidopropanesulfonate; dimethylaminopropyl(meth)acrylamide, alkyl vinyl ethers, vinyl chloride, vinylidene chloride, N-vinylpyrollidone, allyl containing monomers, sulfonates; aromatic vinyl compounds such as styrene, substituted styrenes; butadiene; acrylonitrile; monomers containing acetoacetoxy functional groups such as acetoacetoxyethyl methacrylate; vinyl esters of saturated carboxylic, e.g. acetate, propionate, neodecanoate; acid or base containing monomers such as, for example, (meth) acrylic acid, itaconic acid, maleic acid, fumaric acid, N,N-dimethylaminoethyl methacrylate; or ii) a polymer with a high acid content, for example, a polymer with from 10 to 60% by weight of the polymer of for example, (meth)acrylic acid, preferably from 10 to 50% methacrylic acid and with a Tg in the range from −30 to >100° C. In some cases, this can give a relatively soft outer phase and is not strictly thought of as a "shell". Suitable outer phase polymers of this type are described in EP-A-576128; and U.S. Pat. No. 4,916,171.

iii) polyvinyl alcohol. This alcohol when used as an outer layer is found to stabilise various copolymers with Tg's in the range from −85 to +35° C., for example, vinyl acetate homopolymer; vinyl acetate/ethylene copolymer; vinyl acetate/ethylene/acrylic acid or ester copolymer; vinyl acetate/acrylic acid or ester copolymer such as but not limited to those disclosed in U.S. Pat. Nos. 4,921,898 and 3,827,996.

By "active ingredient" we mean any material which promotes utility of a pellet containing such an active ingredient, in a particular application; for example, the active ingredient may be a material which has activity as a pharmaceutical, an agrochemical, a water treatment agent, a water softening agent, a fabric softening agent, a laundry detergent, a hard surface cleaner, a surface polishing agent, a polish stripping material, a biocide, a stone washing agent or a drain pipe cleaner.

Of particular interest are pellets which contain active ingredients which have activity as a laundry or dishwashing detergent and/or a hard surface cleaner, referred to collectively as detergent-active compounds. The total amount of binder may be from 0.1 to 25% by weight of the pellet, preferably from 0.5 to 15% and particularly preferably from 1 to 5% by weight of the pellet. Such pellets will typically also contain one or more other ingredients which include builders, suitably in an amount of from 5 to 80wt %, preferably from 20 to 80wt %; bleaching agents; processing additives; adjuvants; enzymes; scale inhibitors; emulsifiers; surfactants; soaps; dispersants; zeolites; de-greasing agents; anti-foaming agents; phosphates; phosphonates; optical brighteners; fillers; extenders; soil removers; deflocculating agents; anti-coagulants; anti-drift agents; disintegration agents, including for example, water swellable polymers; water entraining agents, such as, cellulose; plasticizers or coalescing agents, for example, alkylene glycol alkyl ethers, aromatic glycol ethers, alkyl polyglucosides, polysiloxanes, alcohols and alkyl ester acetates; diluents and carriers. Some of these other ingredients will also be applicable for use in non-detergent pellets.

The one or more binders are incorporated within the body of the pellets of the invention by any suitable method. Preferred methods include either i) forming an aqueous slurry of the pellet materials including the one or more binders, spray drying the slurry to give a granular product and then compacting these granules in a pelletising machine to form pellets; or ii) grinding together a dry mixture of the pellet materials including the one or more solid binders and then compacting this mixture in a pelletising machine to form pellets;

iii) spraying the one or more binders into the other pellet materials in powder form and then compacting to form pellets; or iv) dispersing melted binder material into the other pellet materials in solid or powder form and compacting to form pellets.

Typical compacting loads for commercial pellets without the binders of the present invention can be up to 5000 pounds. The binders of the present invention allows the same pellet formulation to be formed using lower compacting loads. The actual compacting load needed will vary depending on the size of the particles, and the composition of the inorganic components of the pellet.

The coating materials are applied to the outer surface of the pellets by any known method, for example, coating with molten material or coating with a solution of the coating material, by dipping, spraying or brush painting. Enhanced pellet strength is achieved if the coating material also comprises a dicarboxylic acid, for example oxalic acid, malonic acid, succinic acid, glutaric acid, adipic acid, pimelic acid, suberic acid, azelaic acid, sebacic acid, undecanedioic acid, dodecanedioic acid, tridecanedioic acid and mixtures thereof. Typically, the amount of coating material applied to a pellet is from 0.1 to 25% by weight of the pellet, preferably from 0.5 to 15% and particularly preferably <5% by weight of the pellet.

The present invention will now be described with reference to the following Examples.

The polymers used in the present invention are detailed in Table I below.

TABLE I

| POLYMER | COMPOSITION | Glass Transition Temperature/° C. |
|---|---|---|
| 1 | crosslinked BA//MMA (core//shell) | −44//+100 |
| 2 | BA/MAA//MMA/MAA + cross-linker (core//shell) | +10//+100 |
| 3 | 98BA/2MAA//85BA/15MAA (multiphase polymer with soft, high acid outer layer) | −40//−15 |
| 4 | 83LMA/5MMA/MAA copolymer | −50 |
| 5 | PVOH stabilised VA/BA/AA copolymer | −12 |

Key:
BA = butyl acrylate
AA = acrylic acid
VA = vinyl acetate
MMA = methyl methacrylate
MAA = methacrylic acid
LMA = lauryl methacrylate
PVOH = polyvinyl alcohol Determination of the Strength of Pellets (Diametrical Fracture Stress)

Diametrical stress fracture, that is, the amount of force applied to the pellet per unit area (KiloPascals) at the point the pellet fractures, was determined by slowly applying a continuously increasing load to a pellet of known diameter and thickness, until compressional failure (fracture). The diametrical fracture stress, X, was calculated according to the equation:

$$X = 2L/dh\pi$$

where L=applied load at point of fracture, d=pellet diameter and h=pellet thickness.

Assessment of the Speed of Dissolution of the Pellets in Water

Each pellet (15 g) was placed in a net and held at the bottom of a beaker. To the beaker was added 400 g of ambient temperature tap water (150 ppm hardness). The water was stirred with an overhead stirrer and the time taken for the pellet to dissolve completely out of the net was determined.

Preparation of Pellets with Polymers of the Present Invention Incorporated Therein as Binder Materials Method 1. Dry Pressing Detergent Granules and Binder Dry polymers at various weight % (as indicated in Table II below) were mixed thoroughly with Tide® detergent granules and placed inside a 2.8 cm diameter cylinder. The piston rod was inserted into the cylinder and the assembly placed between the bottom table and upper plate of a Carver laboratory pellet press. A specified load stress was applied to the pellet for 15 seconds at ambient temperature and the pellet was removed from the cylinder. A range of compacting pressures were used and the effect on diametrical fracture stress and tablet dissolution time (both determined as described above) is also noted in Table II.

TABLE II

| POLYMER | WT % OF POLYMER IN PELLET | COMPACTION LOAD (lbs) | DIAMETRICAL FRACTURE STRESS (kPa) | PELLET DISSOLUTION (mins) |
|---|---|---|---|---|
| Control | none | 250 | 40 | 43 |
| 1 | 1 | 250 | 82 | not measured |
| 1 | 2 | 250 | 99 | 46 |
| 1 | 3 | 250 | 126 | 39 |
| 1 | 2 | 110 | 51 | 32 |
| 1 | 3 | 110 | 68 | 29 |
| 2 | 3 | 250 | 58 | 48 |

The data in Table II shows that polymers used in the present invention increase diametrical fracture stress. This means that pellets may be prepared which are of equal or greater diametrical fracture stress but using lower compacting pressures, compared against pellets prepared without these polymers.

Method 2, Slurry Method

About 10 parts of water were added to 100 parts of detergent granules with mixing. The polymer was added to the resulting slurry and mixed thoroughly. The product was oven dried overnight at 50° C. to give granules which were chopped to approximate uniform size. The resulting dry powder was then pressed into pellets as described above, using the compacting pressures indicated in Table III.

The diametrical fracture stress and dissolution rates for these pellets are noted in Table III below.

TABLE III

| POLYMER | WT % OF POLYMER IN PELLET | COMPACTION LOAD (lbs) | DIAMETRICAL FRACTURE STRESS (kPa) | PELLET DISSOLUTION (mins) |
|---|---|---|---|---|
| Control | none | 250 | 26 | 39 |
| 3 | 0.7 | 250 | 42 | 37 |
| 3 | 1.0 | 250 | 71 | 37 |
| 3 | 1.0 | 100 | 46 | 22 |
| 4 | 2.0 | 250 | 62 | 42 |
| 4 | 2.0 | 100 | 41 | 28 |
| 5 | 2.0 | 100 | 36 | 26 |

The results in Table III indicate that a significant increase in diametrical fracture stress is obtained with the polymers of the present invention and that this is even maintained under a lower compacting load.

Method to Provide an Indication of the Robustness of the Coating Material Containing Polymers of the Present Invention A sample of the coating material was prepared by the following method. To 50 g of molten adipic acid was added dry polymer in the amounts specified in Table IV. The mixture was stirred until the polymer was dispersed, and was allowed to cool at room temperature to give a light orange glassy solid disc of about 1 cm thick and 4 cm in diameter. The impact resistance of the solid disc was tested in two ways—both give an indication as to the robustness of the coating material if it were applied to pellets.

1) The solid coating material disc was pre-weighed and placed in a 16 ounce glass jar with 2 ceramic cylinder shaped objects. The jar was subjected to 8 hours of rotation at constant speed to cause the ceramic objects to impact upon the solid coating material and to cause a degree of crumbling thereof. The remainder of the whole solid coating material was weighed and the results reported in Table IV indicate the weight % of whole coating material remaining.

2) A rubber mallet (2 lb) was allowed to drop onto the solid coating material disc from a height of 2 feet. The extent to which the coating material broke was qualitatively determined.

TABLE IV

| POLYMER | % WEIGHT IN COATING | GLASS JAR TEST (% WHOLE SOLID REMAINING) | RUBBER MALLET TEST |
|---|---|---|---|
| Control | — | 51 | broke |
| 1 | 10 | 85 | broke |
| 1 | 25 | 98 | broke |
| 1 | 40 | 97 | solid did not break |

We claim:

1. Pellet comprising one or more active ingredients; and either one or both of: (a) one or more binders incorporated within the body of the pellet; and (b) one or more coating materials on the surface of the pellet; characterized in that either one or both of the binders and the coating materials comprise one or more polymers having a Tg in the range from −85° C. to +35° C. and, optionally, wherein the coating and/or binder materials comprise at least one multi-phase polymer and further wherein at least one of the phases of the multi-phase polymer has a Tg in the range from −85° C. to +35° C., providing a pellet having improved diametrical fracture stress under lower compaction loads.

2. Pellet according to claim 1 wherein the coating and/or the binder materials comprise at least one polymer having a Tg in the range from −60° C. to +10° C., allowing the pellet to be prepared under a compaction load that is less than 5000 pounds.

3. Pellet according to claim 1 wherein the polymers are insoluble in water and are easily dispersible in water.

4. Pellet according to claim 1 wherein either one or both of the binders and the coating materials comprise polymers comprising polymerized residues of one or more of the following monomers: (meth)acrylic acid, (meth)acrylic esters, a C(1–30) alkyl substituted acrylamide; vinyl sulfonate, acrylamidopropanesulfonate; dimethylaminopropylacrylamide, alkyl vinyl ethers, vinyl chloride, vinylidene chloride, N-vinylpyrollidone, allyl containing monomers, an aromatic vinyl compound; a substituted aromatic vinyl compound; butadiene; acrylonitrile; monomers containing acetoacetoxy functional groups; vinyl esters of saturated carboxylic acids; and acid or base containing monomers.

5. Pellet according to claim 1 wherein the binder and/or the coating materials comprise polymers selected from the group consisting of one of either:

i) a multiphase polymer having at least one inner phase polymer with a Tg in the range from −85 to +35° C. and at least one outer phase polymer with a Tg in the range from +40 to +160° C.; or ii) a multiphase polymer having a inner phase which comprises a polymer with a Tg in the range from −85 to +35° C. and an outer phase with a carboxylic acid content 10 to 60% by weight of the multiphase polymer wherein the outer phase has a Tg in the range from −30 to >100° C.; or iii) a copolymer having a Tg in the range −85 to +35° C. which is stabilised with polyvinyl alcohol.

6. Pellet according to claim 5 wherein the at least one outer phase polymer of the multiphase polymer in part i) comprises polymerized residues of one or more of the following monomers: (meth)acrylic acid, a (meth) acrylate ester; an amide; vinyl sulfonate, acrylamidopropanesulfonate; dimethylaminopropylacrylamide, alkyl vinyl ethers, C(1–30) vinyl esters, vinyl chloride, vinylidene chloride, N-vinylpyrollidone, allyl containing monomers, an aromatic vinyl compound; a substituted aromatic vinyl compound; butadiene; acrylonitrile; monomers containing acetoacetoxy functional groups; and acid or base containing monomers.

7. Pellet according to claim 1 wherein the active ingredient is a material with activity as a pharmaceutical, an agrochemical, a water treatment agent, a water softening agent, a fabric softening agent, a laundry detergent, a hard surface cleaner, a surface polishing agent, a polish stripping material, a biocide, a stone washing agent or a drain pipe cleaner.

8. Pellet according to claim 1 wherein the coating material also comprises a dicarboxylic acid.

9. Method of making a pellet according to claim 1 comprising the steps of:

a) combining pellet materials with binder according to claim 1 by either
   i) forming an aqueous slurry of the pellet materials and the one or more binder materials in water, spray drying the slurry to give a granular product; or
   ii) grinding together a dry mixture of the pellet materials and the one or more binder materials; or
   iii) spraying the one or more binder materials in melted form into the pellet materials in powder form;

b) compacting the resulting pellet material/binder material mixture to form a pellet; and optionally c) applying a coating to the resulting pellet.

10. Method of making a pellet according to claim 1 comprising the steps of compacting pellet materials without binder to form a pellet and coating the pellet with the coating material according to claim 1.

* * * * *